(12) United States Patent
Yamanaka et al.

(10) Patent No.: US 8,220,310 B2
(45) Date of Patent: Jul. 17, 2012

(54) GAS ANALYZER AND METHOD OF GAS ANALYSIS

(75) Inventors: Kazushi Yamanaka, Sendai (JP); Toshihiro Tsuji, Sendai (JP); Naoya Iwata, Sendai (JP)

(73) Assignee: Tohoku University, Sendai-shi (JP)

( * ) Notice: Subject to any disclaimer, the term of this patent is extended or adjusted under 35 U.S.C. 154(b) by 399 days.

(21) Appl. No.: 12/312,307

(22) PCT Filed: May 24, 2007

(86) PCT No.: PCT/JP2007/060599
§ 371 (c)(1),
(2), (4) Date: Jun. 18, 2009

(87) PCT Pub. No.: WO2008/056458
PCT Pub. Date: May 15, 2008

(65) Prior Publication Data
US 2010/0018288 A1 Jan. 28, 2010

(30) Foreign Application Priority Data
Nov. 10, 2006 (JP) ................................ 2006-304650

(51) Int. Cl.
*G01N 30/02* (2006.01)
(52) U.S. Cl. .......................................... 73/23.4
(58) Field of Classification Search .............. 73/24.01, 73/23.4, 24.06, 31.06; 310/313 R, 313 D
See application file for complete search history.

(56) References Cited

U.S. PATENT DOCUMENTS

| | | | | |
|---|---|---|---|---|
| 3,815,056 | A | 6/1974 | Meyer et al. ................. | 333/150 |
| 5,076,094 | A | 12/1991 | Frye et al. .................... | 73/19.03 |
| 5,289,715 | A | 3/1994 | Staples et al. ............... | 73/24.01 |
| 7,170,213 | B2 * | 1/2007 | Yamanaka et al. ........ | 310/313 R |
| 7,647,814 | B2 * | 1/2010 | Nakaso et al. .............. | 73/24.01 |
| 2004/0261497 | A1 | 12/2004 | Thurston et al. ............ | 73/25.03 |
| 2007/0041870 | A1 * | 2/2007 | Yamanaka et al. ......... | 422/58 |

FOREIGN PATENT DOCUMENTS

| | | |
|---|---|---|
| JP | A-5-172795 | 7/1993 |
| JP | A-8-68781 | 3/1996 |

(Continued)

OTHER PUBLICATIONS

Yamanaka et al.; "Precise velocity measurement of surface acoustic waves on a bearing ball;" *Applied Physics Letters*; May 8, 2000; pp. 2797-2799; vol. 76-No. 19.

(Continued)

*Primary Examiner* — Hezron E Williams
*Assistant Examiner* — Tamiko Bellamy
(74) *Attorney, Agent, or Firm* — Oliff & Berridge, PLC

(57) ABSTRACT

A gas analyzer that can be miniaturized and detect a wide variety of gases with high sensitivity, and a method of gas analysis. A separation column is configured so as to pass a sample gas together with a carrier gas through the inside thereof. A surface acoustic wave device has a base material with an annularly continuous annular surface formed of at least a part of a spherical surface; a surface acoustic wave generating means capable of generating a surface acoustic wave that propagates along the annular surface; and a plurality of reaction parts provided along the annular surface so as to change a predetermined physical quantity of the surface acoustic wave in response to the components of the sample gas. The surface acoustic wave device is arranged so that the sample gas passing through the separation column is reacted with the reaction parts. The measuring part can measure a physical quantity of the surface acoustic wave propagating along the annular surface, and the components of the sample gas can be analyzed on the basis of the measured physical quantity.

12 Claims, 4 Drawing Sheets

FOREIGN PATENT DOCUMENTS

| | | |
|---|---|---|
| JP | A-2004-514138 | 5/2004 |
| JP | A-2004-233069 | 8/2004 |
| JP | A-2005-291955 | 10/2005 |
| JP | A-2006-71482 | 3/2006 |
| WO | WO 2004/086028 A1 | 10/2004 |

OTHER PUBLICATIONS

Nakaso et al.; "Diffraction-Free Propagation of Collimated Saw Around a Quartz Ball;" *IEEE Ultrasonics Symposium*; 2002; pp. 47-52.

Yamanaka et al.; "Ultramultiple Roundtrips of Surface Acoustic Wave on Sphere Realizing Innovation of Gas Sensors;" *IEEE Transactions on Ultrasonics, Ferroelectrics, and Frequency Control*; Apr. 2006; pp. 793-801; vol. 53-No. 4.

Iwata et al.; "Analysis of ball SAW sensor response to a wide variety of gases using gas chromatography;" *Symposium on Ultrasonic Electronics Ronbunshu*; Nov. 16, 2006; pp. 367-368; vol. 27. (With Abstract).

Akao et al., "Observation of the Roundtrips of Surface Acoustic Waves on a Single Crystal LiNbO3 Ball", Japanese Journal of Applied Physics, May 2004, pp. 3067-3070. vol. 43, No, 5B, The Japan Society of Applied Physics, Japan.

Yamanaka et al., "Ball Saw Device for Hydrogen Gas Sensor", IEEE Ultrasonics Symposium Proceedings, Oct. 2003, pp. 299-302, vol. 1, IEEE, United States.

European Search Report issued in European Patent Appln. No. 07 74 4033; mailed Jan. 12, 2012.

\* cited by examiner

GAS ANALYZER AND METHOD OF GAS ANALYSIS

BACKGROUND OF THE INVENTION

1. Technical Field

The present invention relates to a gas analyzer using a surface acoustic wave device, and a method of gas analysis.

2. Background Art

Chemical substances in the environment have serious effects on human beings, and there are many kinds of unpredictable hazardous and toxic gases present in living spaces, production sites, transportation facilities, and other areas. Hence, there is a demand for a sensing technique of immediately measuring such gases by a portable compact sensor and setting off alarm. In most cases, no prior information on the kinds of gases present can be obtained. It is therefore necessary to separate and detect more than 100 kinds of various hazardous and toxic gases; gas sensors for detection of only several kinds of specific gases are insufficient. Further, since a gas sensor generally responds to a plurality of gases, a wide variety of gases can hardly be detected even by as many sensors as the number of gases. For this reason, methods using pattern recognition or multivariate analysis of response patterns of several sensors having different gas responses have been proposed. However, when several gases reach the sensors at the same time, such methods using pattern recognition problematically fail to detect the gases.

As stated above, the measurement of simultaneously reaching several gases is difficult for portable sensors, but this measurement is possible by analyzers installed on the floor or table. In particular, a gas chromatograph is a typical example of such analyzers. A gas chromatograph makes use of a phenomenon that when a plurality of gases pass through the inside of a column, e.g., a packed column filled with liquid-coated particles and a capillary column to the inside of which a liquid is applied, the difference in solubility between the gases and the liquid makes a difference in the pass times of the gases; and the gas molecules are detected by a detector disposed at the outlet of the column. A wide variety of gases can be identified and measured by one or a few sensors.

For example, a flat surface acoustic wave (SAW) sensor (see, e.g., Patent Literature 1) is used as a detector for a gas chromatograph. FIG. 7(a) shows a surface acoustic wave sensor 50 comprising an oscillator circuit, in which surface acoustic waves propagate on a base material 51, and then is fed back to an input terminal as electric signals. This sensor is compact in size and easy to arrange in an arrayed shape. In the surface acoustic wave sensor 50, mass loading and elastic loading on a sensitive film 52 due to the influence of gas molecules are measured as changes in frequency (or velocity) of surface acoustic wave.

Meanwhile, the present inventors found that surface acoustic waves traveled along the surface of a ball many times (over 100 times) more than expected. Analyzing the cause, they discovered nondiffracting beams (see Non Patent Literature 1). This is a phenomenon in which surface acoustic waves on a ball are influenced by two effects, i.e., diffraction, as a universal phenomenon of waves, and focusing by the geometric feature of a ball, and as a result of the balance of them, a narrowly collimated (parallel) beam is naturally formed. Thus, the surface acoustic wave is not influenced by obstacles, strains, defects, etc., of portions other than the narrow beam. Therefore, the wavefront is precisely maintained and attenuation is low, permitting multiple rounds of the surface acoustic wave. The inventors also revealed that the conditions for forming non-diffraction beams are such that the width of the beam is equal to the geometric mean of the diameter of a ball and the wavelength of a surface acoustic wave. Here, the influence of diffraction disappears, which is a phenomenon beyond common sense in physics. This is a new fundamental discovery made after over 100 years since the discovery of surface waves by Rayleigh in 1885, and this discovery is useful for great improvement in the sensitivity of the surface acoustic wave device. More specifically, in a spherical surface acoustic wave sensor 60 utilizing this phenomenon, as shown in FIG. 7(b), since a surface acoustic wave propagates for a long distance by multiple rounds, attenuation changes are amplified in proportion to the number of turns, and are thus measurable as amplitude variations (see Non-Patent Literatures 1 through 3). Surface acoustic waves were known to travel along the surface of a cylindroid, cylinder, cone, ball, and the like (see, e.g., Patent Literature 2); however, the above-described facts that surface acoustic waves travel along the surface of a ball, free of influence of diffraction within a band having a predetermined width, and conditions thereof were first found by the present inventors, and have been put to practical use.

SUMMARY OF THE INVENTION

Technical Problem

Columns and detectors of gas chromatographs are large in size, and miniaturization thereof reduces the performance of gas chromatographs. For this problem, no palm-sized and portable gas chromatograph has been put to practical use.

As described in Patent Literature 1, when a flat surface acoustic wave sensor is used as a detector of a gas chromatograph, since the propagation distance of surface acoustic waves is limited by not only the size of the device but also the theoretical limit of waves that amplitude is decreased by diffraction, there is a limit to the enhancement of the accuracy by an increased propagation distance. In addition to this problem, there is another problem that short propagation distance fails to measure attenuation with high accuracy, since amplitude variation of the surface acoustic wave is small even when attenuation varies slightly by the influence of the gas.

In a gas chromatograph, gases are separated by a column; however, it is not easy for a column to separate a poorly soluble gas group with small molecular weight, such as nitrogen and methane contained in a natural gas. Therefore, when two kinds of gas molecules enter into the surface acoustic wave sensor 50 at the same time, as shown in FIG. 7(a), the influences of the two molecules are doubly observed. With only a single measured quantity, i.e., frequency (or velocity), the partial pressures of the two molecules cannot be separated and measured. For the separation of such two kinds of gas molecules, a special column coated with a highly soluble liquid is required, which raises a problem that the apparatus becomes large in size and complicated. Note that this problem is common to surface acoustic wave sensors as well as other detectors for use in a gas chromatograph.

The present invention has focused on these problems and aims to provide a gas analyzer that can be miniaturized and detect a wide variety of gases with high sensitivity, and also provide a method of gas analysis.

Solution to Problem

In order to achieve the above-mentioned object, the gas analyzer according to the present invention comprises a separation column, a surface acoustic wave device, a surface acoustic wave measuring means, and an analysis means; the separation column being configured so as to pass a sample gas together with a carrier gas through the inside thereof, and having different pass times depending on the kinds of components of the sample gas; the surface acoustic wave device comprising a base material with an annularly continuous annular surface formed of at least a part of a spherical surface, a surface acoustic wave generating means capable of generating a surface acoustic wave that propagates along the annular surface, and one or more reaction parts provided along the annular surface so as to change a predetermined physical quantity of the surface acoustic wave propagating along the annular surface generated by the surface acoustic wave generating means, in response to one or more kinds of components of the sample gas, the surface acoustic wave device being arranged so that the sample gas passing through the separation column reacts with the reaction parts; the surface acoustic wave measuring means measuring the physical quantity of the surface acoustic wave propagating along the annular surface generated by the surface acoustic wave generating means; and the analysis means analyzing the components of the sample gas based on the physical quantity measured by the surface acoustic wave measuring means.

The method of gas analysis according to the present invention comprises a column passing step of passing a sample gas together with a carrier gas through the inside of a separation column having different pass times depending on the kinds of components of the sample gas; a surface acoustic wave generating step of generating, on a base material with an annularly continuous annular surface formed of at least a part of a spherical surface, a surface acoustic wave that propagates along the annular surface; a reaction step of changing a predetermined physical quantity of the surface acoustic wave propagating along the annular surface generated in the surface acoustic wave generating step, by reacting the sample gas passing through the separation column in the column passing step, with one or more reaction parts that are provided along the annular surface of the base material and respond to one or more kinds of components of the sample gas; a measuring step of measuring the physical quantity of the surface acoustic wave that has been changed in the reaction step; and an analysis step of analyzing the components of the sample gas based on the physical quantity measured in the measuring step.

According to the gas analyzer and method of gas analysis of the present invention, on a base material with an annularly continuous annular surface formed of at least a part of a spherical surface, a surface acoustic wave that propagates along the annular surface is generated, and thereby the surface acoustic wave is allowed to travel along the annular surface as a nondiffracting beam, leading to the multiple roundtrips. The sample gas passing through the separation column is allowed to react with the reaction parts to change a predetermined physical quantity of the surface acoustic wave. As a result, the multiple roundtrips of the surface acoustic wave can amplify changes in the physical quantity. The amplified changes in the physical quantity of the surface acoustic wave can be measured with high accuracy. Further, since each of the various components of the sample gas is released from the separation column with a different pass time, each component can be separated in terms of time and measured with high accuracy. Thus, the combination of a separation column and a surface acoustic wave device allows for the analysis of the components of a sample gas based on the physical quantity measured with high accuracy, enabling the detection of a wide variety of gases with high sensitivity.

Even when several kinds of components of the sample gas cannot be separated in a separation column, the components can be separated by making use of the fact that velocity and amplitude are mutually independent physical quantities. More specifically, using reaction parts capable of changing attenuation and velocity of surface acoustic waves, amplitude determined by the attenuation of a surface acoustic wave, and delay time determined by the velocity are measured to separate the components. Since there is no need to strictly separate the components of the sample gas by the separation column, the separation column can be simplified and miniaturized. Accordingly, the entire apparatus can be miniaturized into a palm size held in a pocket.

As the separation column, any column may be used as long as it has different pass times depending on the kinds of components of a sample gas. For example, a column of a gas chromatograph may be employed. The reaction part is preferably composed of a thin sensitive film. When using a plurality of reaction parts, each of them preferably responds to a different component.

In the gas analyzer of the present invention, it is preferable that the sample gas comprises several kinds of components; the reaction parts are provided so as to change attenuation and velocity of the surface acoustic wave propagating along the annular surface; the surface acoustic wave measuring means measures amplitude determined by the above attenuation of the surface acoustic wave, and delay time determined by the above velocity; and that the analysis means calculates the partial pressure of each component of the sample gas by determining velocity of the surface acoustic wave from the above delay time measured by the surface acoustic wave measuring means, determining attenuation of the surface acoustic wave from the above amplitude measured by the surface acoustic wave measuring means, and then solving simultaneous equations including the above velocity and the above attenuation and using the partial pressure of each component of the sample gas as a variable.

In the gas analyzer of the present invention, the analysis means may determine attenuation at a plurality of different frequencies of the surface acoustic wave from the above amplitude measured by the surface acoustic wave measuring means, and then calculate the partial pressure of each component of the sample gas based on the above velocity and the attenuation at each frequency.

In the method of gas analysis of the present invention, it is preferable that the sample gas comprises several kinds of components; the reaction step reacts the sample gas with the reaction parts to change attenuation and velocity of the surface acoustic wave; the measuring step measures amplitude determined by the above attenuation of the surface acoustic wave that has been changed in the reaction step, and delay time determined by the above velocity; and that the analysis step calculates the partial pressure of each component of the sample gas by determining velocity of the surface acoustic wave from the above delay time measured in the measuring step, determining attenuation of the surface acoustic wave from the above amplitude measured by the surface acoustic wave measuring means, and then solving simultaneous equations including the above velocity and the above attenuation and using the partial pressure of each component of the sample gas as a variable.

The method of determining the partial pressure of each component of a sample gas based on velocity and attenuation of surface acoustic waves was first found by the present inventors. In particular, the use of attenuation of surface acoustic waves, which was not used before, allows for the detection of a wide variety of gases with high sensitivity. Since amplitude and velocity are mutually independent physical quantities, when measuring amplitude determined by attenuation of a surface acoustic wave and delay time determined by velocity of the surface acoustic wave, the partial pressures of two kinds of components can be calculated on the basis of the attenuation determined by the amplitude and the delay time determined by the velocity, and thereby two kinds of gases can be detected with high sensitivity. Moreover, by determining attenuation at a plurality of different frequencies, the partial pressures of various kinds of components can be calculated on the basis of the velocity and the attenuation at each frequency, and thereby a wide variety of gases can be detected with high sensitivity.

Hereinafter, a method of analyzing a sample gas using the gas analyzer and method of gas analysis of the present invention is theoretically formulated.

First, amplitude of a surface acoustic wave (SAW) after propagation over a distance L is represented by Equation (1).

[Mathematical Expression 1]

$$V = V_0 \exp[-(\alpha_L + \alpha_A)L] \quad (1)$$

$\alpha = \alpha_L + \alpha_A$
$\alpha_L$: leakage attenuation coefficient
$\alpha_A$: attenuation coefficient by absorption and scattering Provided that the base material is spherical, when a film is formed on the surface of the sphere, changes in velocity and attenuation of SAW are represented by Equation (2). Here, the film refers to, when there is a sensitive film, a sensitive film that has absorbed gas molecules; and when there is no sensitive film, an adsorbed layer of gas molecules (which is regarded as a continuum). Further, since P is the power density of SAW, $c_i$ (i=1-3) is independent of the SAW power density, and determined only by the properties of the base material.

[Mathematical Expression 2]

$$\frac{\Delta \gamma}{k_0} = \frac{\Delta \alpha}{k_0} - j\frac{\Delta V}{V_0} = j\omega h \sum_{i=1}^{3} c_i\left(\rho - \frac{E^{(i)}}{V_0^2}\right) \quad (2)$$

$V_0$: SAW velocity of base material
$\Delta V$ change in velocity
$k_0$: SAW wave number of base material
$\Delta \alpha$: change in attenuation coefficient
$\omega$: angular frequency
h: film thickness
$c_i = v_{i0}^2/(4k_0 P)$, $v_{i0} = j\omega u_{i0}$: components in each direction (i=1-3) of particle velocity on the base material surface
P: SAW power density (energy flux per unit beam width)
$\rho$: film density
$E^{(1)} = T_{13}/(2S_{13})$, $E^{(2)} = T_{23}/(2S_{23})$, $E^{(3)} = T_{33}/S_{33}$ film elastic constants
$T_{i3}, S_{i3}$: components of stress and strain tensor of film According to Equation (2), the changes increase in proportion to the film thickness and SAW frequency. The first term of the right-hand side of Equation (2) is mass loading, and the second term is elastic loading. It is shown that a sensitive film with a large change in shear modulus is effective for a crystal plane in which the in-plane displacement is dominant, and that a sensitive film with large change in longitudinal modulus is effective for a crystal plane in which the out-of-plane displacement is dominant. For this reason, in the gas analyzer of the present invention, the base material may comprise an anisotropic crystal; and the reaction parts may have a sensitive film on the annular surface of the base material in a part where the in-plane displacement is larger, said film greatly changing shear modulus in response to the sample gas; and another sensitive film on the annular surface of the base material in a part where the out-of-plane displacement is dominant, said film greatly changing longitudinal modulus in response to the sample gas.

A gas analyzer having no separation column cannot be used for the identification of different molecular because, even when a plurality of sensitive films are provided in a single round path of the base material, the observed responses of the films to the molecules are overlapped. However, in the gas analyzer of the present invention, even when a plurality of sensitive films are formed in a single round path of the base material, each gas is separated in the separation column in terms of time, and then reaches the films. Accordingly, the response of each sensitive film can be identified and observed. For this reason, it becomes crucial to form sensitive films responding to a wide variety of gases on one spherical surface acoustic wave device, enabling the miniaturization of the entire apparatus.

Next, in order to specifically show the behaviors of the gas analyzer and method of gas analysis of the present invention, provided that in Equation (2), only elastic modulus (the third term of the summation on the right-hand side) with respect to displacement in the normal direction is effective, the effect of elastic loading is represented by Equations (3). Further, the leakage attenuation coefficient is approximately represented by Equation (4).

[Mathematical Expression 3]

$$\frac{\Delta \gamma}{k_0} = \frac{\Delta \alpha}{k_0} - j\frac{\Delta V}{V_0} \quad (3)$$

$$= j\omega h c_3\left(\rho - \frac{E' + jE''}{V_0^2}\right)$$

$$= j\omega h c_3\left(\rho - \frac{E'}{V_0^2} - j\frac{E''}{V_0^2}\right)$$

$$\therefore \frac{\Delta \alpha}{k_0} = \frac{\omega h c_3 E''}{V_0^2} \text{ and } \frac{\Delta V}{V_0} = -\omega h c_3\left(\rho - \frac{E'}{V_0^2}\right)$$

$$\alpha_L = \frac{r_C f P}{\rho_S V_S^2}\left(\frac{\gamma M}{RT}\right)^{1/2} \quad (4)$$

f: SAW frequency
P: gas pressure
$\rho_S$: density of sensor base material
$V_S$: SAW velocity
$\gamma$: ratio of specific heat at constant pressure and constant volume (monatomic gas: 1.66, diatomic gas: 1.4)
R: gas constant (8.314 J/(Kmol))
T: absolute temperature
M: molecular weight ($H_2$: 2, He: 4, $N_2$: 28, Ar: 40)
$r_C$: correction factor of about 0.8-0.9 that corrects an error from the experimental value First, the following is an example of a method of determining the partial pressures of two kinds of components of a sample gas, when the two components reach the detector at the same time without being separated. When mass loading is dominant and elastic loading is negligible, or when there is no sensitive film, the increase in attenuation constant and acoustic velocity caused by the gas is represented by Equations (5). If the mass loading is proportional to the gas partial pressure, and $\rho = c_1 P_1 + c_2 P_2$ is satisfied, Equations (6) hold. Organizing them, simultaneous equations shown in Equations (7) relating to the partial pressures $P_1$ and $P_2$ are obtained. Here, $a_1$, $a_2$, $b_1$, and $b_2$ are constants depending on the crystal orientation of the base material, gas type, temperature, SAW frequency, thickness of the sensitive film, etc., and can be determined by theoretical calculation or experimental calibration. Then, measuring changes in velocity and attenuation caused by the sample gas, the left-hand side of Equations (7) are given, and the simultaneous equations in Equations (7) are determined. $P_1$ and $P_2$ are determined by solving the simultaneous equations in Equations (7).

[Mathematical Expression 4]

$$\frac{\Delta\alpha}{k_0} = \frac{r_C P}{\rho_0 V_0}\left(\frac{\gamma M}{RT}\right)^{1/2} \text{ and } \frac{\Delta V}{V_0} = -\omega h(c_1+c_2+c_3)\rho \quad (5)$$

$$\frac{\Delta\alpha}{k_0} = \frac{r_C P_1}{\rho_0 V_0}\left(\frac{\gamma_1 M_1}{RT}\right)^{1/2} + \frac{r_C P_2}{\rho_0 V_2}\left(\frac{\gamma_2 M_2}{RT}\right)^{1/2}$$

and $$\frac{\Delta V}{V_0} = -\omega h(c_1+c_2+c_3)\rho \quad (6)$$
$$= -\omega h(c_1+c_2+c_3)(C_1 P_1 + C_2 P_2)$$

$C_1$, $C_2$: proportionality constant depending on film and gas $$\frac{\Delta\alpha}{k_0} = a_1 P_1 + a_2 P_2 \text{ and } \frac{\Delta V}{V_0} = b_1 P_1 + b_2 P_2 \quad (7)$$

$$a_1 = \frac{r_C}{\rho_0 V_0}\left(\frac{\gamma_1 M_1}{RT}\right)^{1/2}$$

$$a_2 = \frac{r_C}{\rho_0 V_0}\left(\frac{\gamma_2 M_2}{RT}\right)^{1/2}$$

$$b_1 = -\omega h(c_1+c_2+c_3)C_1$$
$$b_2 = -\omega h(c_1+c_2+c_3)C_2$$

Further considering from a general standpoint, it is common that when there is different kinds of components (1, 2, 3, ... i) of a sample gas, mechanisms of SAW attenuation by sensitive films are different, and the exponent $\xi_i$ (i=1, 2, 3 ...) representing frequency dependence of attenuation $f^{\xi_i}$ also varies by the gas species from relaxation absorption type 2 to scattering attenuation type 4. Considering the above, when measuring acoustic velocity and attenuation at the fundamental frequency f and the third harmonic 3f, simultaneous Equations (8) relating to the partial pressures $P_1$, $P_2$, $P_3$, ... are obtained. Since $\xi_1 \neq \xi_2 \neq \xi_3$ holds in general, each equation of (8) is linearly independent. That is, there is no proportionality between the coefficients $a_1 f^{\xi_1}$, $a_2 f^{\xi_2}$, $a_3 f^{\xi_3}$, $a_1(3f)^{\xi_1}$, $a_2(3f)^{\xi_2}$, $a_3(3f)^{\xi_3}$, and $b_1$, $b_2$, $b_3$ of each equation. Then, the partial pressures of three kinds of gases can be determined by solving simultaneous Equations (8).

[Mathematical Expression 5]

$$\frac{\Delta\alpha}{k_0}(f) = a_1 f^{\xi_1} P_1 + a_2 f^{\xi_2} P_2 + a_3 f^{\xi_3} P_3 \quad (8)$$

$$\frac{\Delta\alpha}{k_0}(3f) = a_1(3f)^{\xi_1} P_1 + a_2(3f)^{\xi_2} P_2 + a_3(3f)^{\xi_3} P_3$$

$$\frac{\Delta V}{V_0} = b_1 P_1 + b_2 P_2 + b_3 P_3$$

$\frac{\Delta\alpha}{k_0}(f)$: attenuation coefficient at frequency $f$

In the gas analyzer of the present invention, the reaction parts may be provided so as to change attenuation of the surface acoustic wave propagating along the annular surface; the surface acoustic wave measuring means may measure amplitude determined by the above attenuation of the surface acoustic wave; the analysis means may determine leakage attenuation of the surface acoustic wave from time variation of the above amplitude measured by the surface acoustic wave measuring means, and calculate the partial pressure of each component of the sample gas based on the above leakage attenuation. In this case, the partial pressure of each component of the sample gas can be calculated on the basis of the difference in leakage attenuation between the carrier gas and the sample gas. Therefore, the sensitivity can be controlled by selection of a carrier gas, regardless of the kinds of components of the sample gas.

In the method of gas analysis of the present invention, the column passing step may pass the sample gas using different carrier gases; the reaction step may change attenuation of the surface acoustic wave by reacting the sample gas with the reaction parts for each carrier gas; the measuring step may measure amplitude determined by the above attenuation of the surface acoustic wave that has been changed in the reaction step, with respect to each carrier gas; and the analysis step may determine leakage attenuation of the sample gas from time variation of the above amplitude measured in the measuring step, with respect to each carrier gas, and calculate the partial pressure of each component of the sample gas based on the above leakage attenuation. In this case, contribution of attenuation such as viscoelastic attenuation independent of leakage attenuation can be cancelled, and the amount of leakage attenuation can be calculated more accurately. Therefore, the partial pressure of each component of the sample gas can be calculated with high accuracy.

In the gas analyzer of the present invention, the carrier gas may be composed of helium, and the reaction parts may be provided so as to change the physical quantity of the surface acoustic wave in response to a hydrogen gas. In this case, a thermal conductive detector of a general gas chromatograph cannot detect hydrogen because the heat conductivity of hydrogen is close to that of helium; however, the gas analyzer of the present invention can detect hydrogen. Even when the sample gas contains not only hydrogen but also steam and a wide variety of other gases, hydrogen and the wide variety of gases can be detected with high sensitivity.

The method of determining leakage attenuation when using a plurality of carrier gases is formulized. The attenuation when the sample gas with partial pressure $P_1$ reaches the detector is represented by Equation (9), provided that a part of the carrier gases are replaced by the sample gas, and that the term of elastic loading is also included. When using only a carrier gas 1, Equation (10) holds. Therefore, the increment from this is represented by Equation (11). Considering $V_1 = V_v/S$ ($V_v$ is flow rate), Equation (12) independent of $V_1$ and S is finally obtained. Similarly, when an experiment using a different carrier gas 2 is conducted, Equation (13) holds. Equation (12) is subtracted from Equation (13), and thus the contribution of viscoelastic attenuation is canceled. As a result, Equation (14) is obtained. Equation (14) can be used to determine the correction factor $r_c$ from the attenuation measurement experiment. Next, the contribution of viscoelastic attenuation can be calculated from Equation (9).

Note that, although the right-hand side of Equation (14) is obtained from the equation of state for ideal gas, the van der Waals' equation of state can be used for molecules with intermolecular attractive forces. In addition, for the coefficient of the second term of the right-hand side of Equation (14), calibration curve of experimentally measured leakage attenuation may be used, rather than a theoretical equation.

[Mathematical Expresion 6]

$$\frac{\Delta\alpha_{1S}}{k_0} = \frac{\omega h c_3 E''}{V_0^2} + \frac{P_1 - P_S}{\rho_0 V_0} r_C \left(\frac{\gamma_1 M_1}{RT}\right)^{1/2} + \frac{P_S}{\rho_0 V_0} r_C \left(\frac{\gamma_S M_S}{RT}\right)^{1/2} \quad (9)$$

$$\frac{\Delta\alpha_{1S}}{k_0} = \frac{P_1}{\rho_0 V_0} r_C \left(\frac{\gamma_1 M_1}{RT}\right)^{1/2} \quad (10)$$

$$\delta\frac{\Delta\alpha_{1S}}{k_0} = \frac{\omega h c_3 E''}{V_0^2} - \frac{P_S}{\rho_0 V_0} r_C \left(\frac{\gamma_1 M_1}{RT}\right)^{1/2} + \frac{P_S}{\rho_0 V_0} r_C \left(\frac{\gamma_S M_S}{RT}\right)^{1/2} \quad (11)$$

$$= \frac{\omega h c_3 E''}{V_0^2} + \frac{r_C P_S}{\rho_0 V_0} \left[\left(\frac{\gamma_S M_S}{RT}\right)^{1/2} - \left(\frac{\gamma_1 M_1}{RT}\right)^{1/2}\right]$$

$$\delta\frac{\Delta\alpha_{1S}}{k_0} = \frac{\omega h c_3 E''}{V_0^2} + \frac{r_C P_A v_A}{V_v \Delta t_1 \rho_0 V_0} \left[\left(\frac{\gamma_S M_S}{RT}\right)^{1/2} - \left(\frac{\gamma_1 M_1}{RT}\right)^{1/2}\right] \quad (12)$$

$$\delta\frac{\Delta\alpha_{2S}}{k_0} = \frac{\omega h c_3 E''}{V_0^2} + \frac{r_C P_A v_A}{V_v \Delta t_2 \rho_0 V_0} \left[\left(\frac{\gamma_S M_S}{RT}\right)^{1/2} - \left(\frac{\gamma_2 M_2}{RT}\right)^{1/2}\right] \quad (13)$$

$\frac{\omega h c_3 E''}{V_0^2}$: contribution of viscoelastic attenuation $$\delta\frac{\Delta\alpha_{2S}}{k_0} - \delta\frac{\Delta\alpha_{1S}}{k_0} = \frac{r_C P_A v_A}{V_v \Delta t_2 \rho_0 V_0}\left[\left(\frac{\gamma_S M_S}{RT}\right)^{1/2} - \left(\frac{\gamma_2 M_2}{RT}\right)^{1/2}\right] - \frac{r_C P_A v_A}{V_v \Delta t_1 \rho_0 V_0}\left[\left(\frac{\gamma_S M_S}{RT}\right)^{1/2} - \left(\frac{\gamma_1 M_1}{RT}\right)^{1/2}\right] \quad (14)$$

Next, a measurement method is formulated which determines the gas mixture component fraction from leakage attenuation when a sample composed of a gas mixture is separated in the separation column. For example, the case in which hydrogen with a volume fraction c is contained in nitrogen gas is considered. Provided that the pressure of the carrier gas is $P_1$, the partial pressures of the nitrogen and carrier gas during the detection of nitrogen gas are represented by Equations (15). Further, the partial pressures of the hydrogen and carrier gas during the detection of hydrogen gas are represented by Equations (16). Considering $V_1 = V_v/S$ ($V_v$ is flow rate), Equation (17) holds, which is independent of $V_1$ and S.

[Mathematical Expression 7]

$$P_{N2} = P_1 \frac{l_1}{l}(1-c) \quad (15)$$

$$P_{CaN2} = P_1\left[\left(1 - \frac{l_1}{l}\right)(1-c) + c\right]$$

$$P_{H2} = P_1 \frac{l_1}{l} c \quad (16)$$

$$P_{CaH2} = P_1\left[\left(1 - \frac{l_1}{l}\right)c + (1-c)\right]$$

$l_1$: length of sample gas immediately before flowing out from column l: length of sample gas immediately before flowing out $$l_1 = \frac{v_A P_A}{SP_1}$$

(S: cross section of column,
$v_A$: volume of sample gas at atmospheric pressure)
$l = V_1 \Delta t$ ($V_1$: line velocity of carrier gas,
$\Delta t$: gas duration time)

$$\frac{l_1}{l} = \frac{v_A P_A}{SP_1 V_1 \Delta t} = \frac{v_A P_A}{P_1 V_v \Delta t} \quad (17)$$

The SAW attenuation when only the carrier gas reaches the detector is represented by Equation (18). Provided that the attenuation when the nitrogen gas reaches the detector is the sum of the leakage attenuations of the nitrogen and carrier gas, Equation (19) holds, which is larger by the amount given by Equation (20) than that when only the carrier gas reaches. Here, considering Equation (21), Equation (22) holds.

[Mathematical Expression 8]

$$\frac{\Delta\alpha_{Ar}}{k_0} = \frac{r_C P_1}{\rho_0 V_0}\left(\frac{\gamma_{Ca} M_{Ca}}{RT}\right)^{1/2} \quad (18)$$

$$\frac{\Delta\alpha_{N2}}{k_0} = \frac{r_C P_{CaN2}}{\rho_0 V_0}\left(\frac{\gamma_{Ca} M_{Ca}}{RT}\right)^{1/2} + \frac{r_C P_{N2}}{\rho_0 V_0}\left(\frac{\gamma_{N2} M_{N2}}{RT}\right)^{1/2} \quad (19)$$

$$\delta\frac{\Delta\alpha_{N2}}{k_0} = \frac{P_{CaN2} - P_1}{\rho_0 V_0} r_C\left(\frac{\gamma_{Ca} M_{Ca}}{RT}\right)^{1/2} + \frac{P_{N2}}{\rho_0 V_0} r_C\left(\frac{\gamma_{N2} M_{N2}}{RT}\right)^{1/2} \quad (20)$$

$$P_{CaN2} - P_1 = -P_{N2} = -P_1 \frac{l_1}{l}(1-c) = -\frac{v_A P_A}{V_v \Delta t}(1-c) \quad (21)$$

$$\delta\frac{\Delta\alpha_{N2}}{k_0} = \frac{v_A P_A}{V_v \Delta t \rho_0 V_0 \sqrt{RT}}(1-c)[(\gamma_{N2} M_{N2})^{1/2} - (\gamma_{Ca} M_{Ca})^{1/2}] \quad (22)$$

From Equation (22), the hydrogen gas fraction c can be determined. This method is effective for the measurement of 1 to 100% order gas fraction, and can advantageously control the sensitivity by selection of a carrier gas, regardless of the kind of the sample gas. Another advantage for the measurement is that this method does not depend on the pressure $P_1$ of the carrier gas and the cross section S of a column.

When the hydrogen gas reaches the detector, due to contribution of attenuation other than the leakage to the sensitive film, Equation (23) holds, which is larger by the amount given by Equation (24) than that when using only the carrier gas. Since E" is sensitive to hydrogen, Equation (24) is effective for the measurement of low concentration of hydrogen at a fraction of 1% or less.

[Mathematical Expression 9]

$$\frac{\Delta\alpha_{H2}}{k_0} = \frac{\omega h c E''}{V_0^2} + \frac{r_C P_{CaH2}}{\rho_0 V_0}\left(\frac{\gamma_{Ca} M_{Ca}}{RT}\right)^{1/2} + \frac{r_C P_{H2}}{\rho_0 V_0}\left(\frac{\gamma_{H2} M_{H2}}{RT}\right)^{1/2} \quad (23)$$

$$\delta\frac{\Delta\alpha_{H2}}{k_0} = \quad (24)$$

$$\frac{\omega h c E''}{V_0^2} + \frac{P_{CaH2} - P_1}{\rho_0 V_0} r_C\left(\frac{\gamma_{Ca} M_{Ca}}{RT}\right)^{1/2} + \frac{P_{H2}}{\rho_0 V_0} r_C\left(\frac{\gamma_{H2} M_{H2}}{RT}\right)^{1/2}$$

Note that, this measurement theory uses the approximate theory of leakage attenuation of SAW; however, other continuum theories may be used, and experimental calibration curves may also be used. Further hydrogen gas is used as a sample in the above example; however, the gas analyzer and method of gas analysis according to the present invention can be applied to general gases and fluids, in addition to hydrogen gas. A part or whole of the surface acoustic wave device can be immersed in a liquid to be used in analysis of liquids useful for the biotechnology and medical fields.

Advantages Effects of the Invention

The present invention provides a gas analyzer that can be miniaturized and detect a wide variety of gases with high sensitivity, and also provides a method of gas analysis.

DESCRIPTION OF THE PREFERRED EMBODIMENTS

The following explains embodiments of the present invention with reference to the drawings.

FIGS. 1 through 6 show gas analyzers and methods of gas analysis according to embodiments of the present invention.

Figure 1:
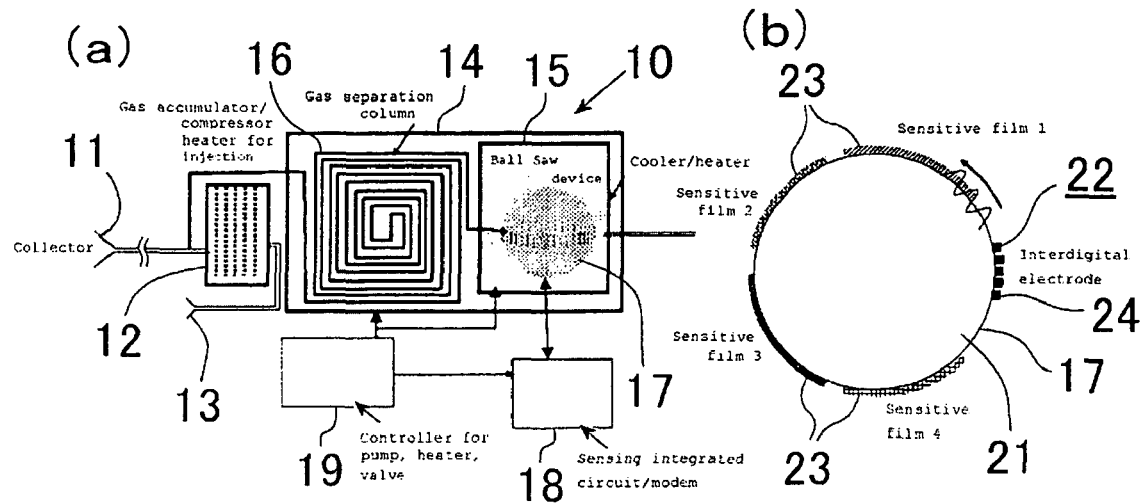
In FIG. 1, (a) is a schematic diagram showing the whole of a gas analyzer and (b) is a cross sectional view of a surface acoustic wave device, according to an embodiment of the present invention.
Figure 2:
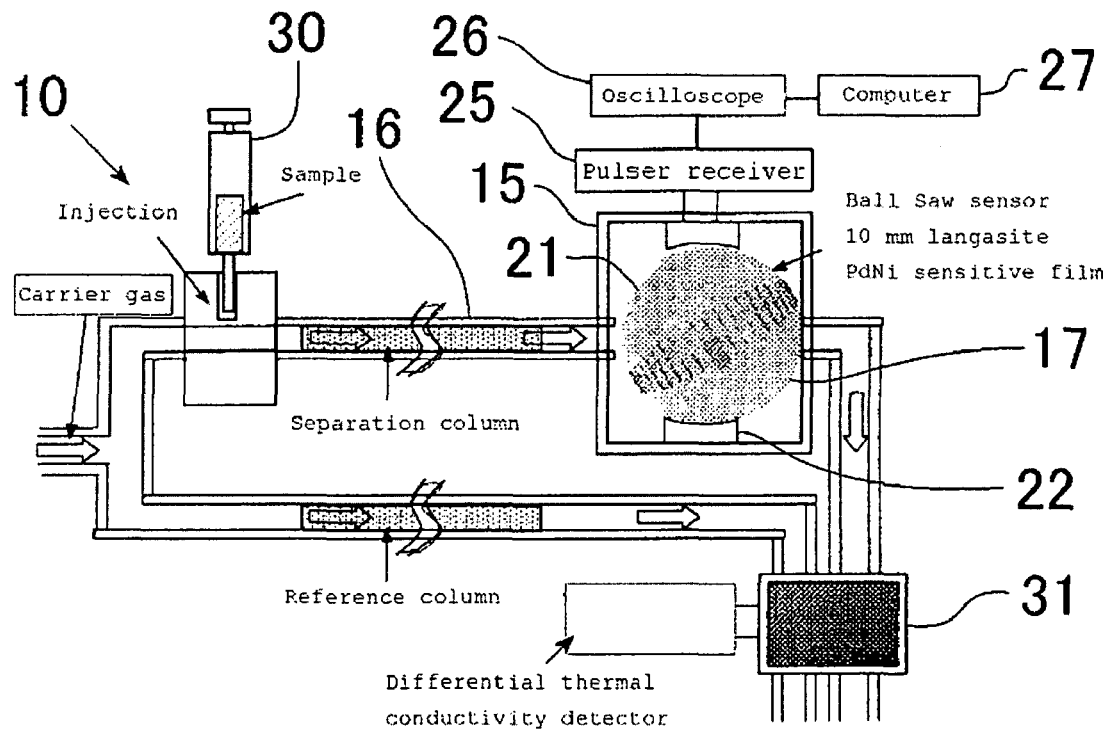
FIG. 2 is a schematic diagram showing the implementation of use of the gas analyzer shown in FIG. 1.

As shown in FIGS. 1 and 2, a gas analyzer 10 has a collector 11, a compressor 12, a carrier gas supplying part 13, a casing 14, a device housing 15, a separation column 16, a surface acoustic wave device 17, a measuring part 18, and a controller 19.

As shown in FIG. 1(a), the collector 11 is configured so as to collect a sample gas by aspiration. The collector 11 is connected to the compressor 12, which can compress and store the sample gas aspirated in the collector 11. The compressor 12 has a heater that can heat the stored sample gas. The compressor 12 is connected to the carrier gas supplying part 13, which can supply a carrier gas with a pump into the compressor 12. The device housing 15 is mounted in the inside of the casing 14.

The separation column 16 is a microfabricated column for a gas chromatograph. The separation column 16 is housed in the casing 14; one end of the column is connected to the compressor 12 outside the casing 14, and the other end is connected to the device housing 15. The separation column 16 is configured so as to pass a sample gas together with the carrier gas through the inside thereof, and has different pass times corresponding to the kinds of components of the sample gas passing through the column.

As shown in FIG. 1, the surface acoustic wave device 17 includes a base material 21, a surface acoustic wave generating means 22, and a plurality of reaction parts 23, and is housed in the device housing 15. The base material 21 is composed of an anisotropic piezoelectric crystal sphere. Thus, the base material 21 has an annularly continuous annular surface formed of a part of the spherical surface. As shown in FIG. 1(b), the surface acoustic wave generating means 22 has an interdigital electrode 24 provided on the surface of the base material 21. Applying a voltage to the interdigital electrode 24, the surface acoustic wave generating means 22 can generate a surface acoustic wave that propagates along the annular surface of the base material 21, due to the piezoelectric effect. In response to the surface acoustic wave propagating along the annular surface, the interdigital electrode 24 can output a voltage corresponding to the waveform of the surface acoustic wave due to the piezoelectric effect.

Each reaction part 23 is composed of a different thin sensitive film that responds to one or more kinds of gas components. Each reaction part 23 is disposed on the annular surface along the path in which the surface acoustic wave generated by the surface acoustic wave generating means 22 propagates. Each reaction part 23 is designed to change attenuation and velocity of the surface acoustic wave propagating along the annular surface in response to the components of the sample gas. Thus, the surface acoustic wave device 17 is configured so that the sample gas supplied in the device housing 15 through the separation column 16 is reacted with the reaction parts 23.

As shown in FIG. 2, the measuring part 18 has a receiver 25, an oscilloscope 26, and a computer 27. The receiver 25 is connected to the interdigital electrode 24 of the surface acoustic wave generating means 22, and can obtain the waveform of the surface acoustic wave propagating along the annular surface via the interdigital electrode 24. The oscilloscope 26 is connected to the receiver 25, and can acquire the waveform of the surface acoustic wave obtained by the receiver 25. The computer 27 is connected to the oscilloscope 26, and can receive the waveform of the surface acoustic wave acquired with the oscilloscope 26; measure amplitude determined by attenuation of the surface acoustic wave, and delay time determined by velocity of the surface acoustic wave; determine attenuation of the surface acoustic wave from the amplitude; determine velocity of the surface acoustic wave from the delay time, and analyze the components of the sample gas based on the attenuation and the velocity. Thus, the measuring part 18 comprises the surface acoustic wave measuring means and the analysis means.

As shown in FIG. 1(a), the controller 19 can control the temperatures in a pump and valve of the carrier gas supplying part 13, the temperature in a heater of the compressor 12, the temperature in the casing 14, the temperature in the device housing 15, and other temperatures.

The method of gas analysis according to an embodiment of the present invention is performed in the following manner using the gas analyzer 10.

First, a sample gas collected by the collector 11 is stored in the compressor 12, and a carrier gas is supplied into the compressor 12. The sample gas in the compressor 12 is rapidly heated by a heater to be introduced, together with the carrier gas, into the separation column 16, and they are allowed to pass through the inside of the separation column 16. Next, the surface acoustic wave generating means 22 generates a surface acoustic wave that propagates along the annular surface of the base material 21. Thereby, the surface acoustic wave can travel along the annular surface of the base material 21 as a nondiffracting beam, leading to multiple roundtrips.

The sample gas passing through the separation column 16 is supplied into the device housing 15, and reacted with, depending on the kinds of the gas components, each reaction part 23 mounted in the base material 21 of the surface acoustic wave device 17. This changes attenuation and velocity of the surface acoustic wave propagating along the annular surface of the base material 21, and also changes amplitude determined by the attenuation and delay time determined by the velocity. Due to multiple rounds of the surface acoustic wave, the changes in amplitude and delay time are amplified. The amplitude and delay time of the surface acoustic wave are measured by the measuring part 18, and the components of the sample gas are analyzed on the basis of the measured amplitude and delay time.

The amplified changes in amplitude and delay time of the surface acoustic wave allow for a high precision measurement of the changes in attenuation and velocity. Moreover, since a wide variety of components of the sample gas are released from the separation column 16 with different pass times, the components can be separated in terms of time and measured with high accuracy. Thus, the components of the sample gas can be analyzed on the basis of the highly accurately measured changes in attenuation and velocity, and thereby a wide variety of gases can be detected with high sensitivity.

Since velocity and attenuation are mutually independent physical quantities, several kinds of components of the sample gas, which cannot be separated even in the separation column 16, can be separated. Thus, there is no need to strictly separate the components of the sample gas in the separation column 16, the separation column 16 can be simplified and miniaturized. Therefore, the entire apparatus can be miniaturized to a palm-size held in a pocket.

When the sample gas contains two kinds of gas components, the partial pressures of the two gas components can be calculated by solving the bivariate simultaneous equations shown in Equations (7), which use the velocity determined from the delay time of the surface acoustic wave and the attenuation determined from the amplitude of the surface acoustic wave. As a result, two kinds of gases can be detected with high sensitivity. When the sample gas contains three or more kinds of gas components, the frequency dependency of the attenuation differs with respect to each gas component, and therefore multivariate simultaneous equations as shown in Equations (8) can be derived. The partial pressures of a wide variety of components can be calculated by determining attenuation at a plurality of different frequencies from the amplitude of the surface acoustic wave, and using the attenuation at each frequency and the velocity to solve the multivariate simultaneous equations. Thereby, a wide variety of gases can be detected with high sensitivity.

In the gas analyzer 10, the reaction parts 23 may have a sensitive film on the annular surface of the base material 21 in a part where the in-plane displacement is dominant, said film greatly changing shear modulus in response to the sample gas; and another sensitive film on the annular surface of the base material 21 in a part where the out-of-plane displacement is dominant, said film greatly changing longitudinal modulus in response to the sample gas. In this case, from Equation (2), the response of each reaction part 23 is more effective, further enhancing the sensitivity of gas analysis.

Moreover, in the gas analyzer 10, the measuring part 18 may be able to determine leakage attenuation of the surface acoustic wave from time variation of the amplitude of the surface acoustic wave, and calculate the partial pressure of each component of the sample gas based on the leakage attenuation. In this case, the partial pressure of each component of the sample gas can be calculated on the basis of the difference in leakage attenuation between the carrier gas and the sample gas. Therefore, the sensitivity can be controlled by selection of a carrier gas, regardless of the kinds of components of the sample gas.

Furthermore, the method of gas analysis and the gas analyzer 10 according to the embodiments of the present invention may calculate the partial pressures of the components of the sample gas as follows. After passing a sample gas using different carrier gases, the measuring part 18 measures amplitude of the surface acoustic wave with respect to each carrier gas; leakage attenuation of the sample gas is determined from time variation of the amplitude with respect to each carrier gas; and the partial pressures of the components of the sample gas are calculated on the basis of the difference in leakage attenuation. In this case, contribution of attenuation such as viscoelastic attenuation independent of leakage attenuation can be cancelled, and the amount of leakage attenuation can be determined more accurately. Therefore, the partial pressures of the components of the sample gas can be calculated with high accuracy.

Figure 3:
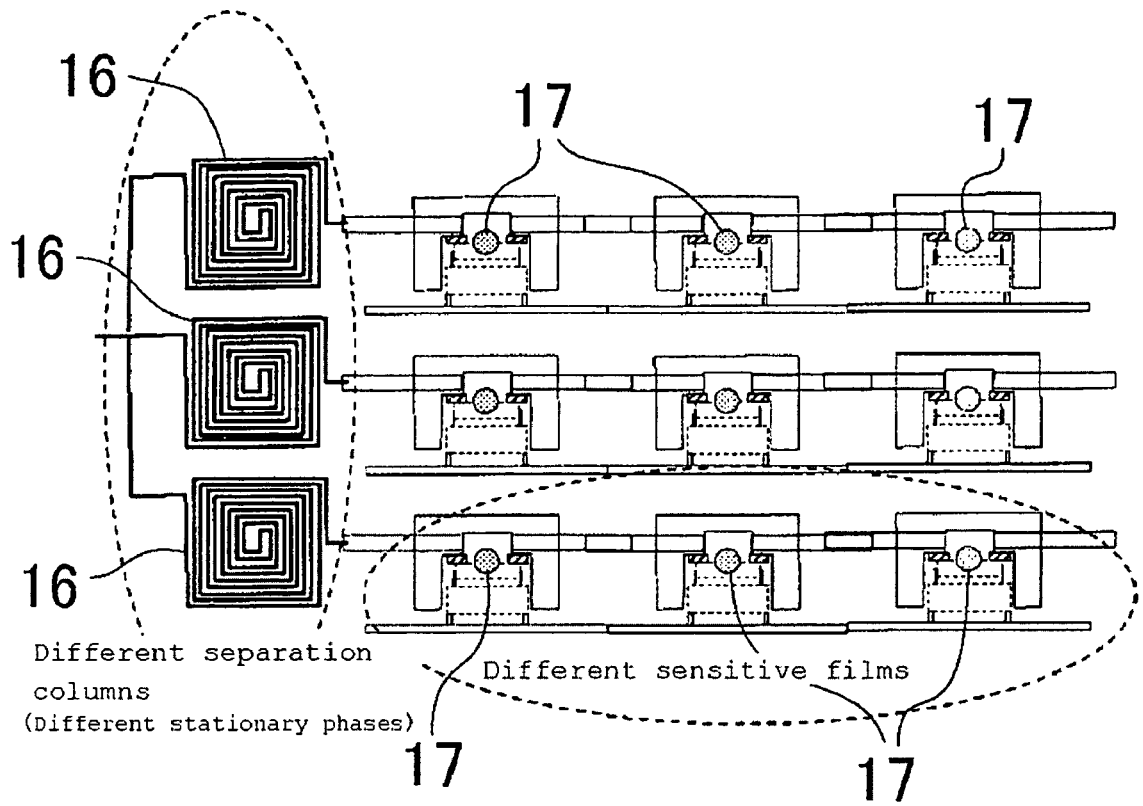
FIG. 3 is a schematic diagram showing a modification of the gas analyzer shown in the FIG. 1, with arrayed separation columns and surface acoustic wave devices.

As shown in FIG. 3, the gas analyzer 10 may include a plurality of separation columns 16 in parallel, which have different stationary phases and can separate different gas components; reaction parts 23 each responding to a different gas component; and a plurality of surface acoustic wave devices 17 connected in series to each separation column 16. In a specific example shown in FIG. 3, there are three separation columns 16, each of which is connected with three surface acoustic wave devices 17. One separation column 16 and one surface acoustic wave device 17 can detect ten kinds of gas components, and the whole of them can detect 90 kinds of gas components. Such an arrayed structure permits analysis of many kinds of gas components. Further, considering that the size of the separation column 16 is about 3 cm×3 cm, and that the size of the base material 21 of the surface acoustic wave device 17 is about 1 mm, a gas analyzer having an arrayed structure can be miniaturized to a palm-size.

Moreover, since the surface acoustic wave device 17 has small fluid resistance and requires no heating, the sample gas may be flowed back to the separation column 16 by back flushing after passing through the surface acoustic wave device 17. Alternatively, another separation column 16 may be provided behind the surface acoustic wave device 17. This can improve the accuracy of separation of gas components by the separation column 16, and thereby enhance the accuracy of analysis of the gas components.

Next, the followings are examples of analyzing various gases making use of the gas analyzer 10 and the method of gas analysis according to the embodiments of the present invention. Helium or argon is used as a carrier gas. The base material 21 is composed of a 10 mm-diameter langasite ball, and the reaction parts 23 are composed of PdNi alloy thin films, which are known to respond to hydrogen gas, water, alcohol, etc. The reaction parts 23 are deposited with a thickness of 20 nm from three directions on the base material 21. The frequency of the surface acoustic wave is 34 MHz, and is measured by the measuring part after 68th turns. As shown in FIG. 2, a sample gas is injected into the separation column by a gas injector 30, and for the confirmation of gas detection by the gas analyzer 10, a differential thermal conductivity detector (TCD) 31 is installed just behind the surface acoustic wave device 17 to measure the gas.

[Measurement of Water-Ethanol Mixture]

Figure 4:
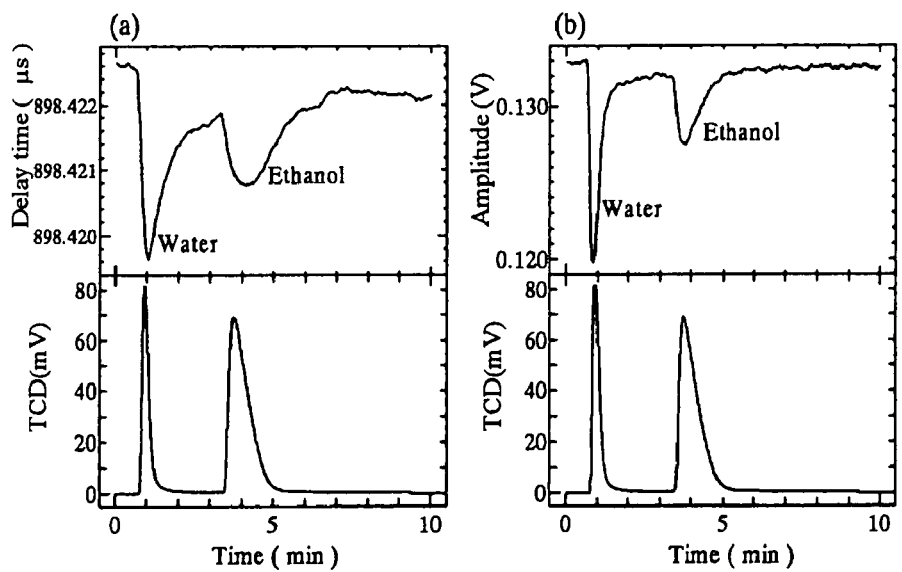
In FIG. 4, (a) shows graphs indicating the response of delay time of the gas analyzer shown in FIG. 1 (upper graph) and that of a thermal conductivity detector (TCD; lower graph), with respect to a water-ethanol gas mixture; and (b) shows graphs indicating the response of amplitude of the gas analyzer shown in FIG. 1 (upper graph) and that of a thermal conductivity detector (TCD; lower graph), with respect to a water-ethanol gas mixture.

FIG. 4 shows the responses of delay time and amplitude to a water-ethanol gas mixture in a ratio of water to ethanol of 1:1. As shown in the upper graphs of FIG. 4(a) and (b), the gas analyzer 10 detected first a response caused by water vapor (water), and secondary a response caused by ethanol vapor (ethanol). As shown in the lower graphs of FIG. 4(a) and (b), TCD 31 also detected responses at the same time as the gas analyzer 10. Note that it took 1 s or less for a gas to flow from the surface acoustic wave device 17 to TCD 31; this time can be ignored in FIG. 4.

As shown in FIG. 4(b) that indicates the amplitude response of the gas analyzer 10, the time constant of the response to the increase and decrease in partial pressure of the gas is almost similar to that of TCD 31, which indicates that real-time responses were obtained. In contrast, as shown in FIG. 4(a), the time constant of the delay time response of the gas analyzer 10 was longer than the time constant of the amplitude response, and the time constant to the partial pressure increase was longer than the time constant to the partial pressure decrease. This result suggests that water molecules and ethanol molecules are absorbed into a PdNi alloy thin film, and that the elastic modulus varies through chemical processes such as dissociation and diffusion. This is useful information for the identification of gas molecules. Thus, there is a possibility that gas molecules are identified by analyzing time variations of velocity and attenuation when the gas partial pressure varies with time to estimate the time constants of processes in which gas molecules are occluded by a sensitive film through absorption, decomposition, and diffusion, and in which the gas molecules are released due to the reduced partial pressure; and then classifying the interaction of the gas molecules with substances from the time constants.

Generally, the difference in time constant between an amplitude response and a delay time response suggests that the mechanisms in which each response occurs are different from each other, meaning that two independent measured quantities can be obtained. Making use of this, even when two kinds of gas molecules are incident on the surface acoustic wave device 17 at the same time, the partial pressures of the two gases can be determined in the following manner. Since velocity and attenuation are controlled by different mechanisms, the relationship between the partial pressures of the gases and the velocity is different from that between the partial pressures and the attenuation. Accordingly, two independently measured quantities are obtained with respect to the gas mixture of two kinds of molecules with unknown partial pressures. As a result, simultaneous equations using the partial pressures of the two gases as two variables are obtained, which can be solved to determine the partial pressures of the two gases.

[Measurement of Various Alcohols]

Figure 5:
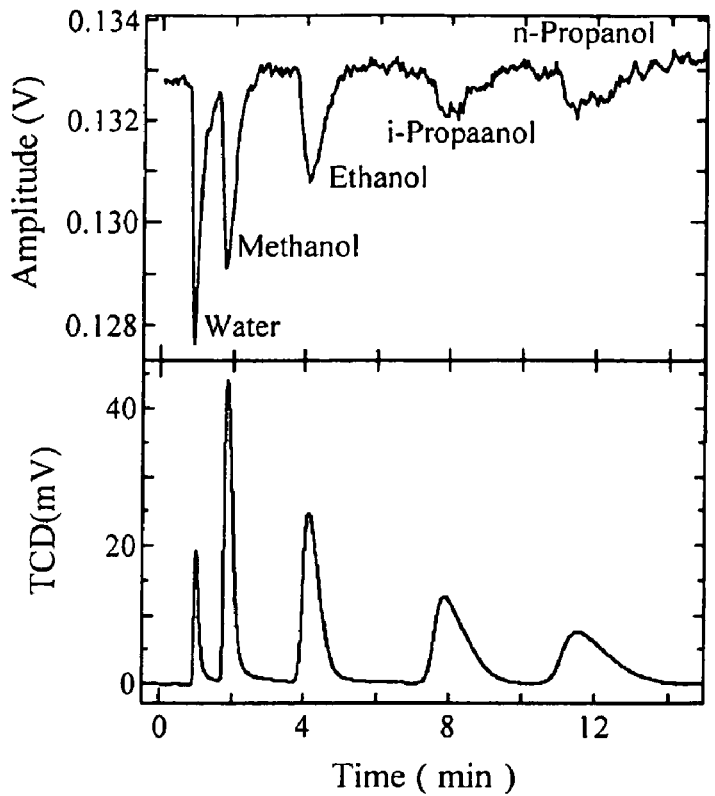
In FIG. 5 shows graphs indicating the response of amplitude of the gas analyzer shown in FIG. 1 (upper graph) and that of a thermal conductivity detector (TCD; lower graph), with respect to a gas mixture of a wide variety of alcohols.

FIG. 5 shows the amplitude response to a gas mixture of methanol, ethanol, 2-propanol (i-propanol), and 1-propanol (n-propanol). The amount of each gas in the mixture is equal, and a small amount of water is contained. As shown in FIG. 5, the amplitude response of the gas analyzer 10 corresponding to the peak of each gas component measured by TCD 31 were observed. The results indicate that the surface acoustic wave device 17 having a PdNi alloy thin film can be used as a detector for a wide variety of alcohol gases.

[Measurement of Hydrogen-Nitrogen Gas Mixture]

Figure 6:
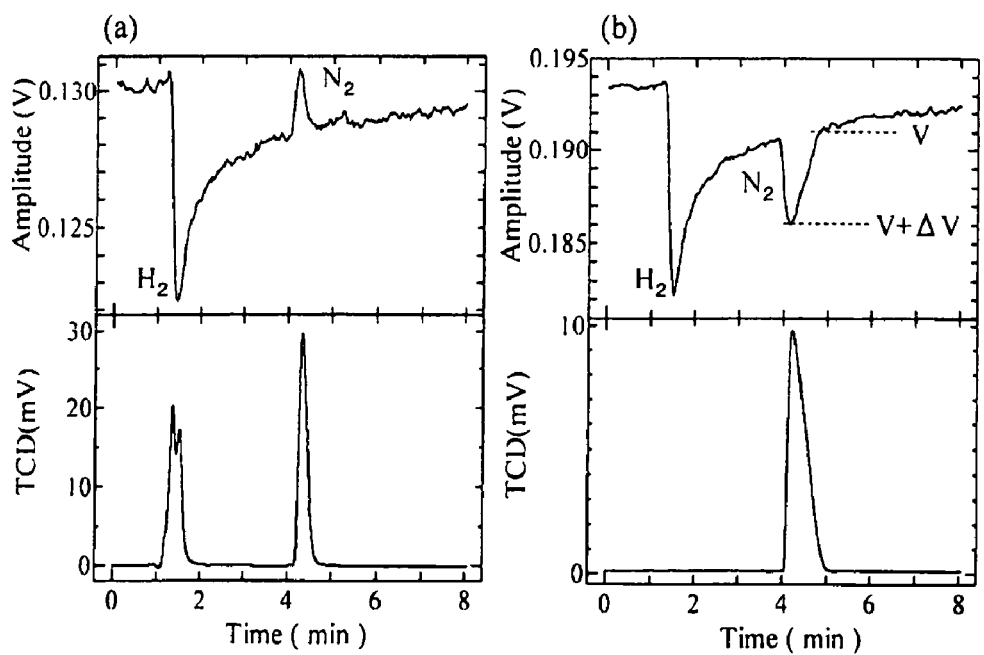
FIG. 6 shows graphs indicating the response of amplitude of the gas analyzer shown in FIG. 1 (upper graph) and that of a thermal conductivity detector (TCD; lower graph), with respect to a 3% hydrogen-nitrogen gas mixture, when the carrier gas was argon (a) and when the carrier gas was helium (b).
Figure 7:
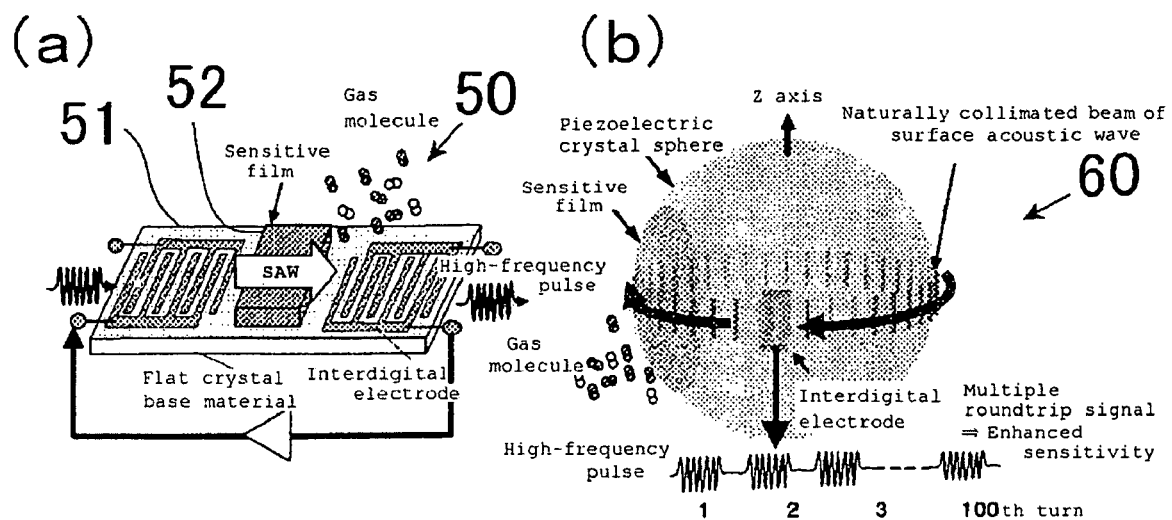
In FIG. 7, (a) shows a perspective view of a flat surface acoustic wave sensor according to prior art, and (b) is a perspective view of a spherical surface acoustic wave according to prior art.

FIG. 6 shows the responses to a 3% hydrogen-nitrogen gas mixture. Both when the carrier gas shown in FIG. 6(a) was argon and when the carrier gas shown in FIG. 6(b) was helium, the amplitude response of hydrogen ($H_2$) was observed. This response is attributed to the occlusion of hydrogen molecules to the PdNi alloy thin film. Further, the surface acoustic wave leaked into the gaseous atmosphere, and since the degree of leakage is specified by the molecular weight of the gas, nitrogen ($N_2$) having a molecular weight different from the carrier gas was also detected, as shown in the upper graphs of FIGS. 6(a) and (b). Moreover, as shown in FIG. 6(b), when the carrier gas was helium, TCD 31 detected no response to the hydrogen because the heat conductivity of hydrogen is close to that of helium; however, the gas analyzer 10 detected. This is an advantage of forming a sensitive film that is sensitive to hydrogen in the round path of the surface acoustic wave device 17.

The following examines quantitative evaluation of nitrogen based on the amount of leakage attenuation of surface acoustic wave.

Given that the leakage attenuation when a nitrogen gas reaches the gas analyzer 10 is the sum of the leakage attenuations of nitrogen and a carrier gas, according to Equation (22), the attenuation $\Delta\alpha_{N2}$ when the nitrogen gas reaches the analyzer is greater by the amount given in Equation (25) than that when only the carrier gas reaches. The correction factor ($r_c$) was set to 1. Moreover, the time variation of the amplitude in n turns during the detection of nitrogen is represented by Equation (26).

[Mathematical Expression 10]

$$\delta \frac{\Delta \alpha_{N2}}{k_0} = \frac{v_A P_A}{V_v \Delta t \rho_0 V_0 \sqrt{RT}} (1-c) \left[ \sqrt{\gamma_{N2} M_{N2}} - \left( \sqrt{\gamma_C M_C} \right) \right] \quad (25)$$

$v_A$: volume of sample gas at atmospheric pressure
$P_A$: atmospheric pressure
$V_r$: gas flow rate
$\Delta t$: gas duration time
c: hydrogen concentration in gas mixture
$\gamma_{N2}, \gamma_C$: ratio of specific heat for nitrogen and carrier gas
$M_{N2}, M_C$: molecular weight of nitrogen and carrier gas $$\Delta V/V = \exp(-\delta \Delta \alpha_{N2} nL) - 1 \quad (26)$$

L: circumference of ball

Table 1 shows the calculation results of the leakage attenuation and the time variation of amplitude (after 1 turn and 68 turns) by Equations (25) and (26), and the experimental values (exp.; after 68 turns), when the carrier gas was argon (Ar) and when the carrier gas was helium (He). Table 1 indicates that multiple roundtrips of the surface acoustic wave on the ball surface is able to measure amplitude change, which cannot be measured by a single round.

TABLE 1

| Carrier gas | $\Delta \alpha$ [1/m] | $\Delta V/V$ 1 turn | $\Delta V/V$ 68 turns | $\Delta V/V$ exp. |
|---|---|---|---|---|
| Ar | −0.0133 | $4 \times 10^{-4}$ | 0.029 | 0.019 |
| He | 0.0183 | $-6 \times 10^{-4}$ | −0.038 | −0.026 |

Comparing the calculation results and experimental value shown in Table 1, the amplitude changes by leakage attenuation are almost equivalent in those of both carrier gases. It was confirmed that Equations (25) and (26) are efficient for quantitative evaluation of leakage attenuation. The cause of errors is assumed that the correction factor was set to 1, and that the flow path of the gas was incomplete; however, the introduction of a correction factor by calibration will possibly allow quantitative analysis of gas by the leakage loss of surface acoustic wave.

Further, it will be possible to identify and quantitatively analyze a plurality of gases, which could not be analyzed by a conventional gas chromatograph due to the overlap of gases, by storing frequency-dependent data of the attenuation by the interdigital electrode 24 that generates a plurality of frequencies, and creating a database.

Although the theory using the approximation theory was disclosed as the theory of leakage attenuation, an expansion using the continuum theory is also easy. Similarly, the theory dealing with mass loading and elastic loading as the effect of the sensitive film was disclosed; however, an expansion dealing with changes in electric conduction is also easy. In addition, the influence of internal friction was cited as the cause of the elastic loading by hydrogen gas; however, it is also possible to handle the influence of changes in electric conduction.

Moreover, as examples of gas detection, the detections of hydrogen, nitrogen, steam, and alcohol were disclosed; however, the kind of gas is not limited thereto. Since there is a considerable accumulation of knowledge about sensitive films, the use of such a sensitive film enables comprehensive detection of hazardous and toxic gases linked to safety and security, such as petroleum-related compounds, aldehydes, ozone precursor hydrocarbons, and chlorofluorocarbons that are ozone depleting substances, as volatile organic compounds; polycyclic aromatic hydrocarbons, PCB, dioxins, phthalate esters, etc., as refractory organic compounds; highly volatile drugs (marijuana, cocaine) and low volatile explosives (Semtex, C4), which are important in the security field; and, as automobile exhausts, NOx, SOx, and other inorganic gases, in addition to petroleum-related compounds.

The present invention can provide a palm-sized and portable gas analyzer. The portable gas analyzer is mainly used and applied in the environmental field that focuses on the analysis of VOC (volatile organic compounds) in air. Typical examples include filed analysis of painting plants, ABS resin plants, petroleum refining plants, and the like; filed analysis of soil contamination investigation (soil gas); working environment measurement in various plants; detection of gas leakage from underground piping of city gas; analysis of gases generated in the case of a fire; etc. For personal use, the gas analyzer may be applied for security checks at airports etc., search for causative substances of chemical sensitivity, formation of environmental information database, and in other environmental fields. Moreover, the spread of the gas analyzer of the present invention will enable construction and sales of time space database of environmental information. Hence, planning service of environmental measures for the administration will be possible, and new industries that significantly contribute to society will possibly be created.

REFERENCE SIGNS LIST

10 Gas analyzer
11 Collector
12 Compressor
13 Carrier gas supplying part
14 Casing
15 Device housing
16 Separation column
17 Surface acoustic wave device
18 Measuring part
19 Controller
21 Base material
22 Surface acoustic wave generating means
23 Reaction parts
24 Interdigital electrode

CITATION LIST

Patent Literature 1

U.S. Pat. No. 5,289,715

Non Patent Literature 1

K. Yamanaka, H. Cho, and Y. Tsukahara, "Precise velocity measurement of surface acoustic waves on a bearing ball," Appl. Phys. Lett., vol. 76, no. 19, pp. 2797-2799, 2000.

Non Patent Literature 2

N. Nakaso, Y. Tsukahara, S. Ishikakwa, and K. Yamanaka, "Diffraction-free propagation of collimated SAW around a quartz ball," Proc. IEEE Ultrason. Symp., pp. 47-50, 2002.

Non Patent Literature 3

K. Yamanaka, S. Ishikawa, N. Nakaso, N. Takeda, D-Y. Sim, T. Mihara, A. Mizukami, I. Satoh, S. Akao, and Y. Tsukahara, "Ultramultiple roundtrips of surface acoustic wave on sphere realizing innovation of gas sensors," IEEE Trans. UFFC., 53(4), 793-801, March, 2006.

Patent Literature 2

U.S. Pat. No. 3,815,056

What is claimed is:

1. A gas analyzer comprising:
a separation column;
a surface acoustic wave device;
a surface acoustic wave measuring means; and
an analysis means;
the separation column being configured so as to pass a sample gas together with a carrier gas through the inside of the column, and having different pass times depending on the kinds of components of the sample gas, the sample gas containing several kinds of components;
the surface acoustic wave device comprising:
a base material with an annularly continuous annular surface formed of at least a part of a spherical surface;
a surface acoustic wave generating means capable of generating a surface acoustic wave that propagates along the annular surface; and
one or more reaction parts provided along the annular surface so as to change attenuation and velocity of the surface acoustic wave propagating along the annular surface generated by the surface acoustic wave generating means, in response to one or more kinds of components of the sample gas;
the surface acoustic wave device being arranged so that the sample gas passing through the separation column reacts with the reaction parts;
the surface acoustic wave measuring means measures amplitude determined by the attenuation of the surface acoustic wave propagating along the annular surface generated by the surface acoustic wave generating means and delay time is determined by the velocity of the surface acoustic wave; and the analysis means analyzing the components of the sample gas based on the amplitude and delay time measured by the surface acoustic wave measuring means, the analysis means determining velocity of the surface acoustic wave from the delay time measured by the surface acoustic wave measuring means, determining attenuation at a plurality of different frequencies of the surface acoustic wave from the amplitude measured by the surface acoustic wave measuring means, calculating the partial pressure of each component of the sample gas based on the velocity and the attenuation at each frequency, and solving simultaneous equations containing the velocity and the attenuation and using the partial pressure of each component of the sample gas as a variable.

2. The gas analyzer according to claim 1, wherein the reaction parts are provided so as to change attenuation of the surface acoustic wave propagating along the annular surface, the surface acoustic wave measuring means measures amplitude determined by the attenuation of the surface acoustic wave, and the analysis means determines leakage attenuation of the surface acoustic wave from time variation of the amplitude measured by the surface acoustic wave measuring means, and calculates the partial pressure of each component of the sample gas based on the leakage attenuation.

3. The gas analyzer according to claim 1, wherein
the base material comprises an anisotropic crystal, and
the reaction parts have a sensitive film on the annular surface of the base material in a part where the in-plane displacement is dominant, the film greatly changing shear modulus in response to the sample gas; and another sensitive film on the annular surface of the base material in a part where the out-of-plane displacement is dominant, the film greatly changing longitudinal modulus in response to the sample gas.

4. The gas analyzer according to claim 1, wherein
the carrier gas comprises helium, and
the reaction parts are provided so as to change the attenuation and velocity of the surface acoustic wave in response to a hydrogen gas.

5. A method of gas analysis comprising:
a column passing step of passing a sample gas together with a carrier gas through the inside of a separation column having different pass times depending on the kinds of components of the sample gas, the sample gas containing several kinds of components,
  a surface acoustic wave generating step of generating, on a base material with an annularly continuous annular surface formed of at least a part of a spherical surface, a surface acoustic wave that propagates along the annular surface;
  a reaction step of changing attenuation and velocity of the surface acoustic wave propagating along the annular surface generated in the surface acoustic wave generating step, by reacting the sample gas passing through the separation column in the column passing step, with one or more reaction parts that are provided along the annular surface of the base material and respond to one or more kinds of components of the sample gas;
  a measuring step of measuring amplitude determined by the attenuation of the surface acoustic wave that has been changed in the reaction step and a delay time determined by the velocity; and an analysis step of analyzing the components of the sample gas based on the amplitude and delay time measured in the measuring step, wherein the analysis step determines the velocity of the surface acoustic wave from the delay time measured in the measuring step, determines the attenuation at a plurality of different frequencies of the surface acoustic wave from the amplitude measured in the measuring step, calculates the partial pressure of each component of the sample gas based on the velocity and attenuation at each frequency, and solves simultaneous equations containing the velocity and the attenuation and using the partial pressure of each component of the sample gas as a variable.

6. The method of gas analysis according to claim 5, wherein
  the column passing step passes the sample gas using different carrier gases,
  the reaction step reacts the sample gas with the reaction parts with respect to each carrier gas to change attenuation of the surface acoustic wave,
  the measuring step measures amplitude determined by the attenuation of the surface acoustic wave which has been changed in the reaction step, with respect to each carrier gas, and
  the analysis step determines leakage attenuation of the sample gas from time variation of the amplitude with respect to each carrier gas, measured in the measuring step, and calculates the partial pressure of each component of the sample gas based on the leakage attenuation.

7. The gas analyzer according to claim 2, wherein
the base material comprises an anisotropic crystal, and
the reaction parts have a sensitive film on the annular surface of the base material in a part where the in-plane displacement is dominant, the film greatly changing shear modulus in response to the sample gas; and another sensitive film on the annular surface of the base material in a part where the out-of-plane displacement is dominant, the film greatly changing longitudinal modulus in response to the sample gas.

8. The gas analyzer according to claim 2, wherein
the carrier gas comprises helium, and
the reaction parts are provided so as to change attenuation of the surface acoustic wave in response to a hydrogen gas.

9. The gas analyzer according to claim 3, wherein
the carrier gas comprises helium, and
the reaction parts are provided so as to change attenuation of the surface acoustic wave in response to a hydrogen gas.

10. The gas analyzer according to claim 7, wherein
the carrier gas comprises helium, and
the reaction parts are provided so as to change attenuation of the surface acoustic wave in response to a hydrogen gas.

11. A gas analyzer comprising:
a separation column;
a surface acoustic wave device;
a surface acoustic wave measuring means; and
an analysis means;
the separation column being configured so as to pass a sample gas together with a carrier gas through the inside thereof, and having different pass times depending on the kinds of components of the sample gas;
the surface acoustic wave device comprising:
a base material with an annularly continuous annular surface formed of at least a part of a spherical surface;

a surface acoustic wave generating means capable of generating a surface acoustic wave that propagates along the annular surface; and one or more reaction parts provided along the annular surface so as to change attenuation of the surface acoustic wave propagating along the annular surface generated by the surface acoustic wave generating means, in response to one or more kinds of components of the sample gas; the surface acoustic wave device being arranged so that the sample gas passing through the separation column reacts with the reaction parts;

the surface acoustic wave measuring means measures amplitude determined by the attenuation of the surface acoustic wave; and the analysis means determines leakage attenuation of the surface acoustic wave from time variation of the amplitude measured by the surface acoustic wave measuring means, and calculates the partial pressure of each component of the sample gas based on the leakage attenuation.

12. A method of gas analysis comprising:

a column passing step of passing a sample gas together with a carrier gas through the inside of a separation column having different pass times depending on the kinds of components of the sample gas, the column passing step passes the sample gas using different carrier gases, a surface acoustic wave generating step of generating, on a base material with an annularly continuous annular surface formed of at least a part of a spherical surface, a surface acoustic wave that propagates along the annular surface, a reaction step of changing attenuation of the surface acoustic wave propagating along the annular surface generated in the surface acoustic wave generating step by reacting the sample gas passing through the separation column in the column passing step with one or more reaction parts, with respect to each carrier gas, that are provided along the annular surface of the base material and respond to one or more kinds of components of the sample gas;

a measuring step of measuring the amplitude determined by the attenuation of the surface acoustic wave which has been changed in the reaction step, with respect to each carrier gas; and an analysis step of analyzing the components of the sample gas based on the attenuation measured in the measuring step, wherein the analysis step determines leakage attenuation of the sample gas from time variation of the amplitude with respect to each carrier gas measured in the measuring step, and calculates the partial pressure of each component of the sample gas based on said leakage attenuation.

* * * * *